United States Patent [19]

Zoller et al.

[11] Patent Number: 4,966,901
[45] Date of Patent: Oct. 30, 1990

[54] PYRROLE DERIVATIVES, THEIR PREPARATION AND THEIR USE AS PHARMACEUTICAL ACTIVE COMPOUNDS

[75] Inventors: Gerhard Zoller, Schöneck; Rudi Beyerle, Frankfurt; Ursula Schindler, Mörfelden-Walldorf, all of Fed. Rep. of Germany

[73] Assignee: Cassella Aktiengesellschaft, Frankfurt, Fed. Rep. of Germany

[21] Appl. No.: 355,993

[22] Filed: May 23, 1989

[30] Foreign Application Priority Data

Jun. 14, 1988 [DE] Fed. Rep. of Germany ....... 3820190

[51] Int. Cl.$^5$ ............... C07D 207/335; C07D 281/06; A61K 31/45; A61K 31/55
[52] U.S. Cl. .................................... 514/211; 514/422; 514/423; 514/427; 514/424; 514/426; 548/518; 548/519; 548/531; 548/532; 548/533; 548/534; 548/537; 548/539; 548/540; 548/541; 548/535; 548/556; 548/557; 548/558; 548/561; 540/524
[58] Field of Search ............... 514/422, 423, 427, 428, 514/211; 540/524; 548/518, 527, 530, 531, 541, 550, 551, 560, 561, 562, 519, 533, 534, 535

[56] References Cited

U.S. PATENT DOCUMENTS 2,805,227  9/1957  Cosulich ............................ 548/531
3,337,562  8/1967  Pesson et al. ...................... 548/539
4,837,225  6/1989  Zoller et al. ....................... 514/428

Primary Examiner—Mukund J. Shah
Assistant Examiner—E. C. Ward
Attorney, Agent, or Firm—Perman & Green

[57] ABSTRACT

Pyrrole derivatives of the general formula I

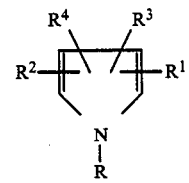

wherein R denotes alkyl which is substituted by —NH$_2$ or acylamino, R$^1$ and R$^2$ independently of one another denote hydrogen or alkyl having 1 to 4 carbon atoms, R$^3$ denotes hydrogen, alkyl having 1 to 4 carbon atoms or a carboxylic acid grouping, R$^4$ denotes a carboxylic acid grouping, nitro, alkylsulphinyl having 1 to 4 carbon atoms, optionally substituted phenylsulphinyl, alkylsulphonyl having 1 to 4 carbon atoms, optionally substituted phenylsulphonyl, alkylcarbonyl having 1 to 6 carbon atoms in the alkyl part, trifluoromethylcarbonyl, optionally substituted phenylcarbonyl, dicyanomethylene, formylvinyl, alkoxycarbonylvinyl having 1 to 6 carbon atoms in the alkoxy part or a carbonyl group, which is substituted by an optionally substituted aliphatic or aromatic 5- to 7-membered heterocyclic radical having 1 or 2 hetero atoms from the series comprising N, O and S, and pharmaceutically acceptable salts or acid addition salts thereof which are useful pharmacological active compounds. The invention also relates to methods for preparing the present compounds. The invention also includes formulations containing effective amounts of such compounds, and methods for administering same to patients for the treatment of diseases caused by restriction in cerebral function and/or for the treatment of cerebral aging processes.

4 Claims, No Drawings

PYRROLE DERIVATIVES, THEIR PREPARATION AND THEIR USE AS PHARMACEUTICAL ACTIVE COMPOUNDS

The present invention relates to pyrrole derivatives of the general formula I

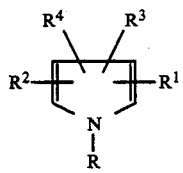

wherein R is alkyl, which is substituted by $-NH_2$ or acylamino of the general formula II

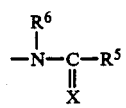

$R^1$ and $R^2$ independently of one another denote hydrogen or alkyl having 1 to 4 carbon atoms, $R^3$ denotes hydrogen, alkyl having 1 to 4 carbon atoms or a carboxylic acid grouping, $R^4$ denotes a carboxylic acid grouping, nitro, alkylsulphinyl having 1 to 4 carbon atoms, optionally substituted phenylsulphinyl, alkylsulphonyl having 1 to 4 carbon atoms, optionally substituted phenylsulphonyl, alkylcarbonyl having 1 to 6 carbon atoms in the alkyl part, trifluoromethylcarbonyl, optionally substituted phenylcarbonyl, dicyanomethylene, formylvinyl, alkoxycarbonylvinyl having 1 to 6 carbon atoms in the alkoxy part or a carbonyl group, which is substituted by an optionally substituted aliphatic or aromatic 5- to 7-membered heterocyclic radical having 1 or 2 hetero atoms from the series comprising N, O and S, $R^5$ denotes hydrogen, optionally substituted alkyl, cycloalkyl having 5 to 7 carbon atoms, optionally substituted phenyl, an optionally substituted aliphatic or aromatic 5- to 7-membered heterocyclic radical having 1 or 2 hetero atoms from the series comprising N, O and S, amino, alkylamino having 1 to 5 carbon atoms or optionally substituted phenylamino, $R^6$ denotes hydrogen or alkyl having 1 to 4 carbon atoms, it also being possible for $R^5$ and $R^6$, together with the

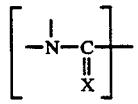

group, to form a ring, and X denotes oxygen or sulphur, and pharmaceutically acceptable salts and acid addition salts thereof which can be prepared.

The invention also relates to processes for the preparation of the compounds of the general formula I and their salts and acid addition salts and to their use as pharmaceutical active compounds.

Alkyl radicals $R^1$, $R^2$ or $R^3$ preferably have 1 to 3 carbon atoms. Methyl is particularly preferred.

The carboxylic acid groupings $R^3$ or $R^4$ preferably denote amides, such as, for example, unsubstituted amide or mono- or dialkylamides having 1 to 3 carbon atoms per alkyl radical, esters, such as, for example, alkyl esters having 1 to 4 carbon atoms per alkyl radical or benzyl esters, the nitrile group or the carboxyl group itself.

Alkyl esters are preferably the methyl ester, the ethyl ester and the tert.-butyl ester.

The optionally substituted aliphatic or aromatic 5- to 7-membered heterocyclic radicals $R^5$ or as a substituent of a carbonyl group $R^4$ contain

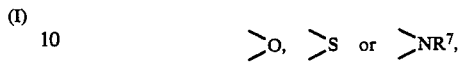

wherein $R^7$ denotes hydrogen, alkyl having 1 to 4, preferably 1 or 2, carbon atoms or alkoxycarbonyl having 1 to 4, preferably 1 or 2, carbon atoms in the alkoxy part, as hetero members.

If the heterocyclic radical contains 2 hetero members, these can be identical or different. A nitrogen-containing heterocyclic radical can also be bonded via the hetero N atom; in addition to the first nitrogen atom which forms the bond, contain any one of the abovementioned hetero members. Examples of such heterocyclic radicals bonded via a hetero N atom are the N-pyrrolidine radical and the N-thiomorpholine radical.

Aromatic heterocyclic radicals are those which can form mesomeric limit structures within the ring on the basis of conjugation of double bonds, if appropriate with free electron pairs, such as, for example, the thienyl radical or the pyrazolyl radical. Aliphatic heterocyclic radicals contain only isolated double bonds, if any, such as, for example, the pyrrolidine radical, the piperidine radical, the morpholine radical or the perhydrothiazepine radical. Of the heterocyclic radicals containing two hetero members, those which contain at least one nitrogen-containing hetero member are preferred.

Examples of heterocyclic compounds from which the heterocyclic radicals $R^5$ or as a substituent of a carbonyl group $R^4$ are derived are: thiophene, di- and tetrahydrothiophene, pyrrole, pyrroline, pyrrolidine, pyridine, dihydropyridine, piperidine, pyran, perhydropyran, oxepine, thiepine, azepine, perhydrooxepine, perhydrothiepine, perhydroazepine, imidazole, imidazoline, imidazolidine, oxazole, oxazoline, oxazolidine, thiazole, thiazoline, thiazolidine, pyrimidine, pyridazine, pyrazine, piperazine, morpholine, thiomorpholine, diazepine, oxazepine, thiazepine and perhydrodiazepine, -oxazepine and -thiazepine.

Particularly preferred heterocyclic radicals are derived from pyrrole, pyrrolidine, imidazole, thiazole, thiazolidine and perhydrothiazepine.

Aliphatic heterocyclic radicals, in particular those which are derived from nitrogen heterocyclic compounds, can also contain a keto function, a double-bonded oxygen atom, on a ring carbon atom, preferably on a ring carbon atom adjacent to the nitrogen-containing hetero member. This keto function can also be in its tautomeric form.

Such a preferred radical is derived, for example, from 5-oxo-perhydro-1,4-thiazepine.

The heterocyclic radicals can also carry a substituent, such as, for example, a carboxyl group, a formyl group, alkoxycarbonyl having 1 to 4, preferably 1 or 2, carbon atoms in the alkoxy group or, preferably, an alkyl group having 1 to 4, preferably 1 or 2, carbon atoms, on one of the ring carbon atoms.

The alkyl radicals of the alkylsulphinyl and alkylsulphonyl groups R⁴ preferably have 1 or 2 carbon atoms.

The alkyl radicals of the alkylcarbonyl and alkoxycarbonylvinyl groups R⁴ preferably have 1 to 3 carbon atoms.

Alkyl R⁵ preferably has 1 to 5 and particularly preferably 1 or 2 carbon atoms and is optionally substituted by —NH₂, monoalkylamino having 1 to 4, preferably 1 or 2, carbon atoms, dialkylamino having a total of 2 to 6, preferably 2 to 4, carbon atoms or an N-pyrrolidinyl, N-piperidinyl, N-morpholinyl or N-thiomorpholinyl radical, or by a piperazin-1-yl radical which is optionally substituted in the 4-position by alkyl having 1 to 4 carbon atoms, phenyl, toluyl, chlorophenyl or methoxy- or ethoxyphenyl, or by alkoxy having 1 to 4, preferably 1 or 2, carbon atoms or by optionally substituted phenoxy.

R⁶ preferably denotes hydrogen.

Rings which R⁵ and R⁶, together with the

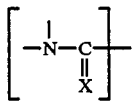

group, can form are advantageously 5- or 6-membered and can optionally be fused to a benzene nucleus. Examples of such rings are 2-pyrrolidinone, 2-piperidinone, 3-oxo-morpholine, 3-oxo-thiomorpholine, phthalimide, 2-oxo-indoline, 1-oxo-isoindoline and 4-methyl-2-oxo-piperazine.

2-Pyrrolidinone is particularly preferred.

A phenylsulphinyl, phenylsulphonyl or phenylcarbonyl radical R⁴ or a phenyl or phenylamino radical R⁵ and a phenoxy radical bonded as a substituent to an alkyl radical R⁵ can in turn carry up to three substituents in the nucleus, and in particular an amino group, monoalkylamino having 1 to 4, preferably 1 or 2, carbon atoms, dialkylamino having a total of 2 to 6, preferably 2 to 4, carbon atoms, alkanoylamino having 1 to 6, preferably 1 or 2, carbon atoms, alkyl having 1 to 4, preferably 1 or 2, carbon atoms, alkoxy having 1 to 4, preferably 1 or 2, carbon atoms, halogen, preferably fluorine, chlorine or bromine, in particular fluorine or chlorine, hydroxyl, nitro, cyano, carboxyl or alkoxycarbonyl having 1 to 4, preferably 1 or 2, carbon atoms in the alkoxy group. A possible optional second substituent of the nucleus is: one of the alkyl or alkoxy groups defined above or one of the abovementioned halogens, and a possible third substituent is one of the above alkyl or alkoxy groups.

An individual substituent can be in the 2-, 3- or 4-position of the phenyl nucleus. In the case of disubstitution, of the possible positions the 2,4-, the 3,4- and the 3,5-position are preferred. In the case of trisubstitution, the positions 2,3,4 and 3,4,5 and 2,4,6 are possible.

Preferred substituents for the phenyl nuclei mentioned are chlorine, alkyl and alkoxy having 1 or 2 carbon atoms, in particular methyl or methoxy, and carboxyl and alkoxycarbonyl having 1 or 2 carbon atoms in the alkoxy group. In addition to the unsubstituted nuclei, the monosubstituted and disubstituted nuclei which carry an alkoxy radical as second substituents are furthermore preferred.

In a toluyl, chlorophenyl or alkoxyphenyl radical bonded to the piperazine group, the substituents can be in the 2-, 3- or 4-position, preferably in the 2- or 4-position, relative to the piperazine radical.

Specific particularly preferred radicals R are alkyl radicals having 1 to 3 carbon atoms, which are substituted by one of the following substituents: formylamino, acetylamino, propionylamino, isopropionylamino, butyrylamino, 4-chlorophenoxyacetylamino, N,N-dimethylamino-acetylamino, L-thiazolidin-4-yl-carbonylamino, 4-chlorobenzoylamino, 5-oxoperhydro-(1,4)-thiazepin3-yl-carbonylamino, aminocarbonylamino, 4-chlorophenylaminocarbonylamino and 2-oxopyrrolidin-1-yl.

Other useful substituents of an alkyl radical R having 1 to 3 carbon atoms are, for example: the amino group, 3,4-dimethoxybenzoylamino, 2-(4-(2-methoxyphenyl)-piperazinyl)-acetylamino, isobutyrylamino, 4-ethoxycarbonylphenylamino-carbonylamino, 4-ethoxycarbonylphenylamino-thiocarbon-ylamino, 4-carboxyphenylamino-carbonylamino and 4-carboxyphenylamino-thiocarbonylamino.

In the general formula I, the radicals R¹, R², R³and R⁴can be on any desired position on the pyrrole nucleus.

Preferably, R⁴ is in the 3-(or 4-)position and R³ is in the 4-(or 3-)position. The radicals R¹ and R² are preferably in the 2- and 5-position.

The compounds of the general formula I according to the invention can be prepared, for example, by electrophilic substitution of pyrroles of the general formula III

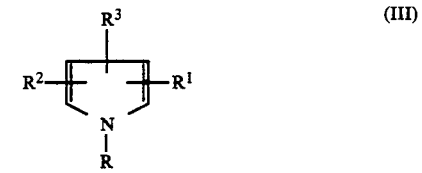

(III)

wherein R, R¹, R² and R³ have the abovementioned meanings, with reagents which introduce the radicals R⁴ into the ring.

Such electrophilic substitution reactions are, for example, Friedel-Crafts acylation (for example J. Org. Chem. 20, 230 (1955), Synth. Commun. 10, 773 (1980)), nitration (Org. Prep. Proced. Int. 19, 48 (1987)), sulphinylation (J. Org. Chem. 45, 5336 (1980)), vinylogous Vilsmeier formylation (Synthesis 1983, 641) or reaction with chlorosulphonyl isocyanate (Synthesis 1985, 355).

Reagents which introduce a radical R⁴ into the ring by electrophilic substitution are, for example, carboxylic acid chlorides, nitronium ions, sulphinic acid chlorides, dimethylaminoacrolein and isocyanates.

The reaction conditions to be observed during the electrophilic substitution, such as, for example, temperature, solvent, molar ratios and catalyst, are known and can be found in the literature references cited above as well as in the usual laboratory handbooks (for example Houben-Weyl).

The compounds of the general formula III are known and can be obtained either by reaction of correspondingly substituted furans with amines of the general formula IV

wherein R has the abovementioned meanings (analogously to U.S. Pat. No. 2,655,512) or by reaction of 1,4-dicarbonyl compounds with amines of the general formula IV (analogous to DE-A No. 35 27 791).

Compounds of the general formula I according to the invention in which $R^4$ denotes dicyanomethylene, alkoxycarbonylvinyl or nitrile can also be prepared by reacting the corresponding aldehyde derivatives with malonodinitrile (Org. Reactions 15, 232 (1967)) or malonic acid esters (Org. Reactions, 15, 229 (1967)) or in a Wittig reaction (J. Org. Chem. 36, 1495 (1971) and Chem. Ber. 88, 1654 (1955)) or with hydroxylamine with subsequent dehydration (Synthesis 1982, 190).

The aldehyde derivatives mentioned can be obtained by formylation of corresponding pyrroles of the general formula III.

Many of the methods described in the literature are suitable formylation reactions (see Houben-Weyl, Methoden der Organischen Chemie (Methods of Organic Chemistry), 4th edition, E3, page 16 et seq. (1983)). In specific cases, the Reimer-Tiemann variant by reaction of the pyrroles with chloroform in an alkaline medium is appropriate, but reactions of the pyrroles with 1,1-dihalogeno ethers and Friedel-Crafts catalysts (J. Med. Chem. 15, 97 (1972) or with trialkoxymethanes and trifluoroacetic acid (J. Org. Chem. 43, 282 (1978)) give better yields. In the simplest case, the Vilsmeier-Haack reaction leads to the compounds according to the invention by reaction of the pyrroles of the general formula III with formamides and phosphorus oxychloride (Methodicum Chimicum 5, page 234 (1975), J. Org. Chem. 28, 3052 (1963)). Phosphorus oxychloride can be replaced by other compounds, such as oxalyl chloride, thionyl chloride, sulphuryl chloride or cyanuric chloride. The reaction is advantageously carried out in the presence of a solvent, such as dimethylformamide, 1,2-dichloroethane or ethers. Isonitriles in acid solution are also suitable formylating agents for the compounds according to the invention (Chem. Ber. 94, 298 (1961)).

However, the corresponding aldehydes can also be obtained directly, analogously to U.S. Pat. No. 2,655,512, from the furanaldehydes and the corresponding amines.

Pyrrolecarboxylic acid derivatives according to the invention can also be obtained directly by reaction of aliphatic 1,4-dicarbonyl compounds of the general formula V

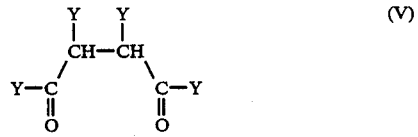

wherein the radicals $R^1$, $R^2$, $R^3$ and $R^4$ are Y, depending on the desired end product, with amines of the general formula IV. An alternative to this reaction is the reaction between correspondingly substituted 2-halogenoketones, β-keto esters and primary amines of the general formula IV (J. Am. Chem. Soc. 73 357 (1951)).

These reactions are usually carried out in suitable solvents at temperatures from 20° to 150° C., preferably below 100° C. and in particular at 40° to 20° C., the starting components usually being employed in approximately equimolar amounts.

If desired, for example if particularly low-boiling solvents are used, the reaction can also be carried out under pressure above the boiling point of the reaction mixture.

Suitable solvents are, for example, alcohols, in particular those having 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those having 2 to 8 C atoms in the molecule, such as, for example, diethyl ether, methyl ethyl ether, di-n-propyl ether, diisopropyl ether, methyl n-butyl ether, ethyl propyl ether, dibutyl ether, tetrahydrofuran, 1,4-dioxane, 1,2-dimethoxyethane and bis-β-methoxyethyl ether; polyethers, such as, for example, polyethylene glycols having a molecular weight of up to about 600; oligoethylene glycol dimethyl ethers, such as, for example, pentaglymes; aliphatic carboxylic acids, in particular formic and acetic acid; glycols and partly etherified glycols, such as, for example, ethylene glycol, propylene glycol, trimethylene glycol, ethylene glycol monomethyl ether, ethylene glycol monoethyl ether and diethylene glycol monoethyl ether; aliphatic hydrocarbons, such as, for example, low- and high-boiling petroleum ether; aromatic hydrocarbons, such as, for example, benzene, toluene and o-, m- and p-xylene; halogenated aliphatic or aromatic hydrocarbons, such as, for example, methylene chloride, chloroform, carbon tetrachloride, chlorobenzene and dichlorobenzene; nitriles, such as, for example, acetonitrile; amides, such as, for example, dimethylformamide and N-methyl-pyrrolidone; hexamethylphosphoric acid triamide; sulphoxides, such as, for example, dimethyl sulphoxide; and water. Mixtures of various solvents can also be used.

The amine of the general formula IV can also be employed in the form of an acid addition salt. The batches are worked up by customary methods. If appropriate, the reaction can also be carried out in the presence of a base or a base mixture. Suitable bases are, for example, tertiary aliphatic amines, such as, for example, triethylamine, tri-n-propylamine and tri-iso-propylamine, and furthermore pyridine, as well as alkali metal carbonates and bicarbonates.

The amines of the general formula IV are known or can easily be prepared by the methods customary for the preparation of primary amines.

The 1,4-dicarbonyl compounds of the general formula V are also known and/or can be prepared by known processes, thus, for example, in accordance with the method of Stetter, Angew. Chem. 88 695 (1976).

By splitting off the acyl radical from compounds of the general formula I according to the invention in which R is an alkyl radical which is substituted by the group of the general formula II

the corresponding compounds according to the invention in which the alkyl radical R is substituted by a primary amino group can be obtained. The acyl radical is split off hydrolytically in a manner which is known per se. For this, the compounds are treated with water or an aqueous organic medium in the presence of molar amounts of a base. The treatment, time depends on the temperature chosen. The reaction can be carried out at room temperature or, in order to accelerate the hydrolysis, at elevated temperature, advantageously up to the reflux temperature of the liquid hydrolysis medium.

The nature of the base to be added is in principle irrelevant. These reagents should merely bring about a sufficiently high OH⊖ concentration and allow easy working up of the batches. These agents can therefore be selected in a known manner.

To prepare the compounds of the general formula I according to the invention in which R is an alkyl radical which is substituted by an acylamino group of the general formula IIa

it is also possible for aminoalkylpyrroles according to the invention, of the general formula Ia

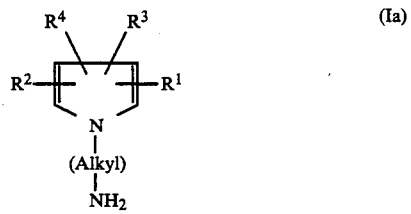

to be acylated with reactive carboxylic acid derivatives derived from carboxylic acids of the general formula VI

wherein $R^5$ has the abovementioned meaning, or with alkali metal cyanate or thiocyanate or with isocyanates or isothiocyanates of the general formula VII

wherein Z denotes oxygen or sulphur and $R^7$ denotes alkyl having 1 to 5 carbon atoms or phenyl, which is optionally substituted in the manner specified above.

Suitable reactive carboxylic acid derivatives are carboxylic acid esters, carboxylic acid anhydrides, carboxylic acid chlorides or carboxylic acids which are activated in situ, such as, for example, with dicyclohexylcarbodiimide (Houben Weyl 8, 522); oxalyl chloride (GB No. 2,139,225); N,N-carbonyldiimidazole (J.Med.-chem. 1982, 620; Synthesis 1982, 833; Chem.Pharm..Bull. 32, 5044 (1984)); N,N'-carbonyldiazoles (Bull. Chem. Soc. Jap. 57, 3597 (1984)); di-(2-pyridyl) carbonate (Tetrahedron Lett. 25, 4943 (1983)); chloroformic acid esters (Tetrahedron Lett. 24, 3365 (1983)); diphosphorus tetraiodide (Chem. Lett. 1983, 449); dialkyl disulphite (Indian J. Chem. 21, 259 (1982)); or methylethylphosphinic anhydride or with other reactive agents.

If isocyanates or isothiocyanates of the formulae $R^7$—NCO and $R^7$—NCS are used as acylating agents, those pyrrole derivatives according to the invention in which R is an alkyl radical substituted by the group —HN—CO—NH—$R^7$ or —NH—CS—NH—$R^7$ are obtained. Reaction of the compounds of the general formula Ia according to the invention with alkali metal cyanates or thiocyanates gives compounds according to the invention in which R is an alkyl radical which is substituted by the groups —NH—CO—NH$_2$ or —NH—CS—NH$_2$.

The reactions are advantageously carried out in the liquid phase, the presence of an inert solvent being advantageous.

If enantiomerically pure carboxylic acid derivatives or compounds of the general formula Ia according to the invention are employed, the compounds of the formula I according to the invention can also be obtained as enantiomerically pure compounds.

If the compounds of the general formula I according to the invention contain basic radicals, they form acid addition salts with inorganic or organic acids. Inorganic and organic acids are suitable for the formation of such acid addition salts. Suitable acids are, for example: hydrochloric acid, hydrobromic acid, naphthalenedisulphonic acids, in particular naphthalene-1,5-disulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared in the customary manner by combining the components, advantageously in a suitable solvent or diluent. The acid addition salts may initially be obtained in the course of working up during synthesis of the compounds of the formula I. If desired, the free compounds of the general formula I can be obtained from the acid addition salts in a known manner, for example by dissolving or suspending in water and rendering the solution or suspension alkaline, for example with sodium hydroxide solution, and subsequent isolation.

Compounds of the general formula I in which $R^3$ and/or $R^4$ is a carboxyl group can also be in salt form. Sodium, potassium and ammonium salts are preferred and can be obtained by reaction of the acid form with corresponding based. If the compounds of the general formula I also contain a free amino group in the radical R, in addition to a carboxyl group, they can also be in the form of inner salts.

The compounds of the general formula I according to the invention and their pharmaceutically acceptable acid addition salts have useful pharmacological properties. They have a central action, for example they exhibit encephalotropic and nootropic actions, and are used for the treatment of diseases of cerebral functions, such as cerebral insufficiency, cerebral ageing processes and reduced memory capacity, such as also occur with Alzheimer's disease or multi-infarct dementia or with reduced learning capacity. Surprisingly, they are considerably superior to the previously known compounds of the same type of action. They exhibit an excellent activity in various types of tests, such as, for example, in prolonging of the survival time under sodium nitrite hypoxia in accordance with the method of Gibsen and Bless (J. Neurochemistry 27, (1976)) and in improving nitrogen-induced hypoxia tolerance, experimental animals being respirated with pure nitrogen after premedication with the preparations investigated and the increase in the time between the start of respiration and electrical neutrality of the electroencephalogram and also the lethality being measured.

The products according to the invention also have a very good action in tests targeted directly towards determination of learning and memory performance, such as, for example, the known "avoidance" tests.

Testing in the tests mentioned and in a number of other tests, such as, for example, the γ-butyrolactone test, shows that low doses of the compounds according to the invention have a low toxicity and surprisingly exhibit a particularly favourable action profile which does not exist in this form in known preparations.

The compounds of the general formula I and their physiologically tolerated salts thus represent an enrichment of pharmacy.

The compounds of the general formula I according to the invention and the abovementioned compounds and their pharmaceutically acceptable acid addition salts can therefore be used on humans as medicines, for example in combating or preventing diseases which are caused by a restriction in cerebral function, and in the treatment and prevention of cerebral ageing processes.

The compounds of the general formula I and the abovementioned compounds and their pharmaceutically acceptable acid addition salts can be administered as medicines by themselves, as mixtures with one another or in the form of pharmaceutical formulations which allow enteral or parenteral use and which contain, as the active constituent, an effective dose of at least one compound of the general formula I or of the abovementioned compounds or of an acid addition salt thereof, in addition to customary pharmaceutically acceptable excipients and additives. The formulations usually contain about 0.5 to 90% by weight of the therapeutically active compound.

The medicines can be administered orally, for example in the form of pills, tablets, lacquered tablets, coated tablets, granules, hard and soft gelatine capsules, solutions, syrups, emulsions or suspensions or aerosol mixtures. However, administration can also be effected rectally, for example in the form of suppositories, or parenterally, for example in the form of injection solutions, or percutaneously, for example in the form of ointments or tinctures.

The pharmaceutical preparations are prepared in a manner which is known per se, pharmaceutically inert inorganic or organic excipients being used. To prepare pills, tablets, coated tablets and hard gelatine capsules, for example, lactose, maize starch or derivatives thereof, talc, stearic acid or salts thereof and the like can be used. Excipients for soft gelatine capsules and suppositories are, for example, fats, waxes, semi-solid and liquid polyols, natural or hardened oils and the like. Suitable excipients for the preparation of solutions and syrups are, for example, water, sucrose, invert sugar, glucose, polyols and the like. Suitable excipients for the preparation of injection solutions are, for example, water, alcohols, glycerol, polyols, vegetable oils and the like.

The pharmaceutical preparations can also contain, in addition to the active compounds and excipients, additives such as, for example, fillers, extenders, disintegrating agents, binders, lubricants, wetting agents, stabilizers, emulsifiers, preservatives, sweeteners, colouring agents, flavouring or aromatizing agents, thickeners, diluents or buffer substances, or furthermore solvents or solubilizing agents or agents for achieving a depot effect, as well as salts for modifying the osmotic pressure, coating agents or antioxidants. They can also contain two or more compounds of the formula I or their pharmacologically acceptable acid addition salts and in addition one or more other therapeutically active substances.

Such other therapeutically active substances are, for example, circulation-promoting agents, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronary dilators, such as carbocromen, dipyridamol, nifedipine and perhexiline, antianginal compounds, such as isosorbide dinitrate, isosorbide mononitrate, glycerol nitrate, molsidomine and verapamil, and β-blockers, such as propranolol, oxprenolol, atenolol, metoprolol and penbutolol. The compounds can moreover be combined with other substances having a nootropic action, such as, for example, piracetam, or substances with an action on the central nervous system, such as pirlindole, sulpiride and the like.

The dosage can vary within wide limits and is to be adapted to the individual circumstances in each specific case. In general, a daily dose of about 0.1 to 1 mg/kg, preferably 0.3 to 0.5 mg/kg of body weight is appropriate for oral administration to achieve effective results, and for intravenous administration the daily dose is generally about 0.01 to 0.3 mg/kg, preferably 0.05 to 0.1 mg/kg of body weight. The daily dose is usually divided into several, for example 2, 3 or 4, part administrations, especially where larger amounts are administered. If appropriate, depending on the individual circumstances, it may be necessary to deviate upwards or downwards from the stated daily dose. Pharmaceutical preparations usually contain 0.1 to 50 mg, preferably 0.5 to 10 mg, of active compound of the general formula I or of a pharmaceutically acceptable salt thereof per dose.

The following Examples 1 to 31 relate to the preparation of compounds of the general formula I, and Examples A to H relate to the preparation of formulations of compounds of the general formula I.

Example 1:

Methyl 1-(2-acetylaminoethyl)-2,4-dimethylpyrrole-3-carboxylate 71.5 g (0.70 mol) of (2-acetylaminoethyl)-amine are slowly added to 40.7 g (0.35 mol) of methyl acetoacetate. 32.4 g (0.35 mol) of chloroacetone are then added dropwise and the mixture is heated under reflux for 20 hours. After cooling, water is added, the mixture is extracted with methylene chloride and the extract is concentrated. The residue is recrystallized from ethyl acetate (filtered over active charcoal and silica gel).

Yield: 37.0 g (44% of theory). Melting point: 130°–132° C. Elemental analysis: $C_{12}H_{18}N_2O_3$ (238.29). Calculated: C 60.5; H 7.6; N 11.8; O 20.1; Found: C 60.8; H 7.7; N 11.9; O 19.8.

Example 2:

Benzyl 1-(2-acetylaminoethyl)-2,4-dimethylpyrrole-3-carboxylate

Obtained analogously to Example 1 by reaction of chloroacetone, 2-acetylaminoethylamine and benzyl acetoacetate.

Melting point: 115°–117° C.

Example 3:

Benzyl 1-(2-acetylaminoethyl)-2,5-dimethylpyrrole-3-carboxylate 7.1 g (0.029 mol) of benzyl acetonylacetoacetate and 3.0 g (0.029 mol) of 2-(acetylaminoethyl)-amine are heated under reflux in 100 ml of isopropanol for 2 hours. The mixture is concentrated, the residue is taken up in dilute hydrochloric acid and the mixture is extracted with methylene chloride. The resulting oil (8.3 g) is chromatographed over a silica gel column using methylene chloride and the product is recrystallized from dibutyl ether.

Yield: 5.1 g (56% of theory); Melting point: 82°–84° C.

Example 4:

Methyl 1-(2-acetylaminoethyl)-2,4,5-trimethylpyrrole-3-carboxylate

By reaction of methyl acetoacetate with 3-chloro-2-butanone and 2-acetylaminoethylamine analogously to Example 1.

Melting point: 163°–165° C.

Example 5:

tert.-Butyl 1-(2-acetylaminoethyl)-2,4,5-trimethylpyrrole-3-carboxylate

By reaction of tert.-butyl acetoacetate with 3-chloro-2-butanone and 2-acetylaminoethylamine analogously to Example 1.

Melting point: 159°–160° C.

Example 6:

1-(2-Acetylaminoethyl)-2,5-dimethylpyrrole-3-carboxylic acid 2.4 g (7.6 mmol) of benzyl 1-(2-acetylaminoethyl)-2,5-dimethylpyrrole-3-carboxylate from Example 3 are dissolved in 200 ml of ethanol and hydrogenated in the presence of 0.5 g of 10% strength Pd-on-charcoal at room temperature. After the mixture has been concentrated, the resulting solid is stirred with methylene chloride and filtered off with suction.

Melting point: 223°–224° C.

Example 7:

1-(2-Acetylaminoethyl)-2,4-dimethylpyrrole-3-carboxylic acid

Analogously to Example 6, the corresponding acid is obtained from benzyl 1-(2-acetylaminoethyl)-2,4-dimethylpyrrole-3-carboxylate (Example 2).

Melting point: 165°–167° C.

The following further compounds according to the invention can be prepared by processes analogous to those described so far:

Example 8

Methyl 1-(3-acetylaminopropyl)-2,5-dimethylpyrrole-3-carboxylate,

Example 9

Ethyl 1-(4-acetylaminobutyl)-2,5-dimethylpyrrole-3-carboxylate,

Example 10

Propyl 1-(2-propionylamino-1-methylethyl)-pyrrole-2-carboxylate,

Example 11

Methyl 1-(2-formylaminoethyl)-pyrrole-3-carboxylate

Example 12

Benzyl 1-(2-benzoylaminopropyl)-2,5-dimethylpyrrole-3-carboxylate.

Example 13:

1-(2-Acetylaminoethyl)-2,5-dimethylpyrrole-3-carbonitrile 5.2 g (0.025 mol) of 1-(2-acetylaminoethyl)-2,5-dimethylpyrrole-3-aldehyde, 1.75 g (0.025 mol) of hydroxylamine hydrochloride and 2 ml (0.025 mol) of pyridine are heated under reflux in 25 ml of toluene for 1.5 hours. After the mixture has been concentrated, the residue is taken up in water, the mixture is extracted with methylene chloride and the product is recrystallized from toluene.

Yield: 3.45 g (67% of theory). Melting point: 131°–133° C. Elemental analysis: $C_{11}H_{15}N_3O$ (205.26). Calculated: C 64.4; H 7.4; N 7.8; O 20.5; Found: C 64.3; H 7.1; N 8.0; O 20.5.

The precursor is obtained in the following way:

15.5 ml (0.166 mol) of phosphorus oxychloride are slowly added dropwise to 13 ml (0.168 mol) of anhydrous dimethylformamide at 0° C. The mixture is stirred at 10° C. for 15 minutes, 70 ml of 1,2-dichloroethane are added and 29.4 g (0.163 mol) of 1-(2-acetylaminoethyl)-2,5-dimethylpyrrole in 25 ml of 1,2-dichloroethane are then added dropwise at 5° C. The mixture is stirred at room temperature for 6 hours, 79.5 g (0.97 mol) of sodium acetate in 130 ml cf water are added, the mixture is heated under reflux for 15 minutes, the phases are separated and the organic phase is concentrated.

The residue is boiled up with toluene and the product which has precipitated is filtered off and recrystallized from ethyl acetate.

Example 14:

1-(2-Acetylaminoethyl)-2,5-dimethylpyrrol-3-yl-methylenemalonodinitrile 4.2 g (0.02 mol) of 1-(2-acetylaminoethyl)-2,5-dimethylpyrrole-3-aldehyde (see Example 13) and 1.35 g (0.02 mol) of malonodinitrile are dissolved in 40 ml of ethanol. After addition of 1 drop of 10 per cent strength potassium hydroxide solution, the mixture is stirred at room temperature for 20 hours and the product is filtered off with suction and recrystallized from isopropanol.

Yield: 3.1 g (60% of theory). Melting point: 184°–185° C. Elemental analysis: $C_{14}H_{16}N_4O$ (256.31). Calculated:

C 65.6; H 6.3; N 21.9; O 6.2; Found: C 65.4; H 6.4; N 21.7; O 6.6.

Example 15:

Methyl 3-(1-(2-acetylaminoethyl)-2,5-dimethylpyrrol-3-yl)-2propenoate 6.1 g (0.05 mol) of monomethyl malonate are dissolved in 20 ml of pyridine. After addition of 10.4 g (0.05 mol) of 1-(2-acetylaminoethyl)-2,5-dimethylpyrrole-3-aldehyde (see Example 13) and 1 ml of piperidine, the mixture is heated under reflux for 15 hours. After addition of a further 27 g of monomethyl malonate, heating is continued for a further 24 hours, the mixture is concentrated, the residue is taken up in water, the mixture is extracted with methylene chloride and the methylene chloride phase is washed with dilute acid and alkali and concentrated. Column chromatography with methylene chloride:methanol=98:2 as the mobile phase gives 7.5 g of product, which can be recrystallized from ethyl acetate.

Yield: 6.5 g (49% of theory). Melting point: 144°-145° C. Elemental analysis: $C_{14}H_{20}N_2O_3$ (264.32). Calculated: C 63.6; H 7.6; N 10.6; O 18.2; Found: C 63.9; H 7.1; N 10.3; O 18.4.

Example 16:

1-(2-Acetylaminoethyl)-2,5-dimethylpyrrole-3,4-dicarbodinitrile 9.0 g (0.05 mol) of 1-(2-acetylaminoethyl)-2,5-dimethylpyrrole are dissolved in 50 ml of acetonitrile. After dropwise addition of 10.5 ml (0.12 mol) of chlorosulphonyl isocyanate in 15 ml of acetonitrile at $-10°$ C., the mixture is subsequently stirred at room temperature for 12 hours and 4.2 ml of dimethylformamide are added dropwise at 0° C. After 1 hour at 50° C., the mixture is poured onto ice and extracted with methylene chloride and the extract is concentrated and chromatographed over a short silica gel column.

Yield: 2.3 g (20% of theory). Melting point: 197°-199° C. Elemental analysis: $C_{12}H_{14}N_4O$ (230.27). Calculated: C 62.6; H 6.1; N 24.3; O 6.9; Found: C 62.2; H 6.3; N 24.1; O 7.5.

Example 17:

3-(1-(2-Acetylaminoethyl)-2,5-dimethylpyrrol-3-yl)-2-propenaldehyde 16.2 g (0.09 mol) of 1-(2-acetylaminoethyl)-2,5-dimethylpyrrole and 10 g (0.1 mol) of 3-dimethylaminoacrolein are dissolved in 80 ml of 1,2-dichloroethane. 9 ml (0.098 mol) of phosphorus oxychloride are added dropwise at $-10°$ C. After 20 minutes, 41 g (0.5 mol) of sodium acetate in 150 ml of water are added, the mixture is stirred at room temperature for 18 hours and heated at 70° C. for 2 hours, the phases are separated, the organic phase is chromatographed over a silica gel column and the product is recrystallized from isopropanol.

Yield: 2.3 g (11% of theory). Melting point: 186°-187° C. Elemental analysis: $C_{13}H_{18}N_2O_2$ (234.30). Calculated: C 66.6; H 7.7; N 12.0; O 13.7; Found: C 66.4; H 7.8; N 11.7; O 13.8.

Example 18:

1-(2-Acetylaminoethyl)-2,5-dimethyl-3-nitropyrrole 18.0 g (0.1 mol) of 1-(2-acetylaminoethyl)-2,5-dimethylpyrrole are introduced into 54 ml of concentrated sulphuric acid at $-10°$ C., during which the temperature rises to 9° C. After the mixture has been subsequently stirred for 5 minutes, 10.9 g (0.11 mol) of potassium nitrate are introduced at about 5° C. After further stirring for 30 minutes, the mixture is poured onto 300 g of ice and extracted with methylene chloride, the extract is concentrated and the residue is chromatographed over a short silica gel column.

Yield: 4.3 g (19% of theory).
Melting point: 155°-157° C.;
Elemental analysis: $C_{10}H_{15}N_3O_3$ (225.25). Calculated: C 53.3; H 6.7; N 18.7; O 21.3; Found: C 53.7; H 6.5; N 19.0; O 21.3.

Example 19:

(1-(2-Acetylaminoethyl)-2,5-dimethyl-3-trifluoroacetyl-pyrrole 8.1 g (0.045 mol) of 1-(2-acetylaminoethyl)-2,5-dimethylpyrrole in 60 ml of toluene are added dropwise to 7 ml (0.05 mol) of trifluoroacetic anhydride in 10 ml of toluene at $-5°$ C. After 20 hours at room temperature, the mixture is hydrolyzed with sodium bicarbonate solution and the product is filtered off with suction and recrystallized from ligroin.

Yield: 6.8 g (55% of theory). Melting point: 128°-130° C. Elemental analysis: $C_{12}H_{15}N_2O_2F_3$ (276.26). Calculated: C 52.2; H 5.5; N 10.1; F 20.6; Found: C 51.9; H 5.3; N 9.9; F 21.0.

Example 20:

3-Acetyl-1-(2-acetylaminoethyl)-2,5-dimethylpyrrole 13.7 g (0.1 mol) of anhydrous zinc chloride are dissolved in 100 ml of ether and the solution is added to 18.0 g (0.1 mol) of 1-(2-acetylaminoethyl)-2,5-dimethylpyrrole and 9.5 ml (0.1 mol) of acetic anhydride in 50 ml of ether. After 1 hour at room temperature, 50 ml of ethylene glycol dimethyl ether are added and stirring is continued for 20 hours. After the hydrolysis, the organic phase is concentrated, the residue is chromatographed and the product is recrystallized from ethyl acetate.

Yield: 4.5 g (20% of theory). Melting point: 136°-138° C. Elemental analysis: $C_{12}H_{18}N_2O_2$ (222.29). Calculated: C 64.8; H 8.2; N 12.6; O 0 14.4; Found: C 65.0; H 8.0; N 12.5; O 14.5.

Example 21:

1-(2-Acetylaminoethyl)-3-benzoyl-2,5-dimethyl-pyrrole

Analogously to Example 20, with benzoic anhydride instead of acetic anhydride.
Melting point: 152°-154° C.

Example 22:

1-(2-Acetylaminoethyl)-2,5-dimethyl-3-(2-pyrrolecarbonyl)-pyrrole

Analogously to Example 20, by acylation with pyrrole-2-carbonyl chloride.
Melting point: 169°-171° C.

Example 23:

1-(2-Acetylaminoethyl)-2,5-dimethyl-3-methylsulphinylpyrrole 19.7 g (0.2 mol) of methylsulphinyl chloride are dissolved in 500 ml of methylene chloride. 36.0 g (0.2 mol) of 1-(2-acetylaminoethyl)-2,5-dimethylpyrrole and 27.6 ml (0.2 mol) of triethylamine in 500 ml of methylene chloride are added dropwise at 0° C. and the mixture is stirred at 0° C. for 45 minutes and poured onto aqueous sodium bicarbonate solution. The organic phase is separated off and discarded. The aqueous phase is concentrated and the residue is boiled up with isopropanol and, after the mixture has been concentrated, the product is chromatographed.

Yield: 9.4 g (19% of theory). Melting point: 113°–115° C. Elemental analysis: $C_{11}H_{18}N_2O_2S$ (242.34). Calculated: C 54.5; H 7.5; N 11.6; O 3.2; Found: C 54.7; H 7.2; N 11.5; O 13.3.

Further compounds according to the invention can be prepared analogously to the examples described above, for example:

Example 24

Benzyl 1-(3-acetylaminopropyl)-2,5-dimethylpyrrole-3-carboxylate

Melting point: 75°–76° C.

Example 25

Benzyl 1-(2-butyrylaminoethyl)-2,5-dimethylpyrrole-3-carboxylate

Melting point: 92°–93° C.

Example 26

2,5-Dimethyl-1-(2-(2-oxo-pyrrolidin-1-yl)-ethyl)-pyrrole-3-carbonitrile

Example 27

1-(2-Formylaminoethyl)-2,5-diethyl-3-phenylsulphonylpyrrole

Example 28 tert.-Butyl 1-(4-aminocarbonylamino-butyl)-2,5-dimethylpyrrole-3-carboxylate

Example 29

1-(2-(5-Oxo-perhydro-1,4-thiazepine-3-carbonyl)-amino)-ethyl-2-propyl-pyrrole-5-carbonitrile

Example 30

Ethyl 1-(2-(3,4-dimethoxybenzoylamino)-ethyl)-2,5-dimethyl-pyrrole-3-carboxylate

Example 31

1-(2-Acetylaminoethyl)-2,5-dimethylpyrrole-3-carboxamide

Melting point: 180°–182° C.

Example 32 tert.-Butyl 1-(2-acetylaminoethyl)-2,5-dimethylpyrrole-3-carboxylate

Melting point: 124°–125° C.

Example 33

2,5-Dimethyl-1-(2-(2-oxopyrrolidin-1-yl)-ethyl)-pyrrole-3-carboxylic acid

Melting point: 199°–201° C.

Example 34

1-(2-Aminoethyl)-2,5-dimethylpyrrole-3-carboxylic acid

Melting point: 195°–196° C.

Example 35

Benzyl 1-(2-benzyloxycarbonylamino-ethyl)-2,5-dimethylpyrrole-3-carboxylate

Melting point: 96°–98° C.

Example 36

1-(2-n-Butyrylamino-ethyl)-2,5-dimethylpyrrole-3-carboxylic acid

Melting point: 170°–171° C.

Example 37

1-(3-Acetylaminopropyl)-2,5-dimethylpyrrole-3-carboxylic acid

Melting point: 175°–176° C.

Example 38

1-(3-Acetylaminopropyl)-2,5-dimethylpyrrole-3-carboxamide

Melting point: 162°–165° C.

Example A

Emulsions containing 3 mg of active compound per 5 ml can be prepared in accordance with the following recipe:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2 g |
| Aroma substances | q.s. |
| Water (demineralized or distilled) | to 100 ml |

Example B

Tablets can be prepared in accordance with the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example C

The following composition is suitable for the preparation of soft gelatine capsules containing 5 mg of active compound per capsule:

| | |
|---|---|
| Active compound | 5 mg |
| Mixture of coconut oil triglycerides | 150 mg |
| Capsule content | 155 mg |

Example D

The following formulation is suitable for the preparation of coated tables:

| Active compound | 3 mg |
|---|---|
| Maize starch | 100 mg |
| Lactose | 55 mg |
| Secondary calcium phosphate | 30 mg |
| Soluble starch | 3 mg |
| Magnesium stearate | 5 mg |
| Colloidal silicic acid | 4 mg |
| | 200 mg |

Example E

Coated tablets containing an active compound according to the invention and another therapeutically active substance:

| Active compound | 6 mg |
|---|---|
| Propranolol | 40 mg |
| Lactose | 90 mg |
| Maize starch | 90 mg |
| Secondary calcium phosphate | 34 mg |
| Soluble starch | 3 mg |
| Magnesium stearate | 3 mg |
| Colloidal silicic acid | 4 mg |
| | 270 mg |

Example F

Coated tablets containing an active compound according to the invention and another therapeutically active substance:

| Active compound | 5 mg |
|---|---|
| Pirlindole | 5 mg |
| Lactose | 60 mg |
| Maize starch | 90 mg |
| Secondary calcium phosphate | 30 mg |
| Soluble starch | 3 mg |
| Magnesium stearate | 3 mg |
| Colloidal silicic acid | 4 mg |
| | 200 mg |

Example G

Capsules containing an active compound according to the invention and another therapeutically active substance:

| Active compound | 5 mg |
|---|---|
| Nicergoline | 5 mg |
| Maize starch | 185 mg |
| | 195 mg |

Example H

Injection solutions containing 1 mg of active compound per ml can be prepared in accordance with the following recipe:

| Active compound | 1.0 mg |
|---|---|
| Polyethylene glycol 400 | 0.3 mg |
| Sodium chloride | 2.7 mg |
| Water for injection purposes to | 1 ml |

The following results, for example, were obtained during pharmacological testing:

Nitrite hypoxia on mice

In this test, cerebral hypoxia leading to massive behavioural disturbances of the animals is produced in mice with $NaNO_2$ (175 mg/kg subcutaneously) by the method of Gibson and Blass (J. Neurochem. 27, 27 (1976)). It is determined whether the ability to hold a rotating bar is influenced by premedication with the test substance. The compounds according to the invention are administered perorally in this test. The results are shown in Table 1.

TABLE 1

Percentage reversal in the disturbance in holding ability following administration of 175 mg/kg of $NaNO_2$ subcutaneously and premedication with the compounds of the general formula I.

| Compounds of the general formula I according to Example | Dose mg/kg (p.o.) | Percentage reversal of the hypoxia effect |
|---|---|---|
| 1 | 0,3 i.p. | 61 |
| 3 | 3 | 62 |
| 4 | 3 | 37 |
| 5 | 3 | 91 |
| 6 | 3 | 57 |
| 13 | 3 | 49 |
| 14 | 3 | 40 |
| 15 | 0,3 | 53 |
| 16 | 1 | 59 |
| 17 | 3 | 30 |
| 18 | 0,3 | 33 |
| 19 | 0,3 | 48 |
| 20 | 0,3 | 55 |
| 21 | 0,3 | 47 |
| 23 | 3 | 75 |
| 24 | 30 | 63 |
| 25 | 3 | 53 |
| 32 | 10 | 62 |
| 33 | 30 | 45 |
| 35 | 3 | 38 |
| 36 | 3 | 61 |
| 37 | 3 | 80 |
| 38 | 30 | 40 |
| Comp. Piracetam | 10 | 19 |

"Passive avoidance"

The test apparatus is a light/dark box with a grid floor which can be electrified in the dark section.

55 minutes after administration of the control and preparation injection, inexperienced male mice are treated with scopolamine hydrobromide (3 mg/kg intraperitoneally). 5 minutes later, the mice are placed in the light section of the box. After moving over into the dark section of the box, they are given an electric shock in the feet which is unpleasant to them. After 24 hours, each mouse is placed once in the light section of the test apparatus and the residence time (maximum 180 seconds) is measured. The animals treated with an active dose of a preparation and scopolamine show a long residence time, as do the animals which have not been treated with scopolamine, whereas those treated with a control injection and scopolamine show a short residence time. The compounds according to the invention are administered in this test in a dose of 10 to 30 mg/kg perorally. The results are shown in Table 2. In this test, a dose of 60 mg/kg perorally of the known compound piracetam achieves a percentage attenuation of 100% (18% at 30 mg/kg perorally).

TABLE 2

Percentage attenuation in the scopolamine-induced amnesia, detectable by an increase in the length of time before entering the dark section of the passive avoidance test space.

| Compounds of the general formula I according to Example | Dose mg/kg (p.o.) | Percentage increase |
|---|---|---|
| 1 | 10 | 39 |
| 3 | 10 | 109 |
| 4 | 30 | 142 |
| 6 | 1 i.p. | 282 |
| 13 | 30 | 37 |
| 14 | 30 | 60 |
| 16 | 10 | 114 |
| 17 | 10 | 114 |
| 18 | 10 | 107 |
| 19 | 10 | 30 |
| 23 | 10 | 125 |
| Comp. Piracetam | 30 | 18 |

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

We claim:

1. Pyrrole compounds of the general formula I

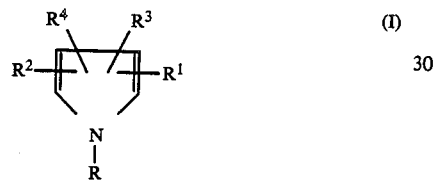

wherein

R is alkyl, which is substituted by —NH₂, or acylamino of the general formula II

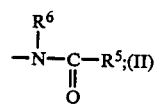

$R^1$ and $R^2$ independently of one another denote hydrogen or alkyl having 1 to 4 carbon atoms;

$R^3$ denotes hydrogen, alkyl having 1 to 4 carbon atoms, an amide, such as, for example, an unsubstituted amide or a mono- or dialkylamide having 1 to 3 carbon atoms per alkyl radical, an ester, such as, for example, an alkyl ester having 1 to 4 carbon atoms per alkyl radical or a benzyl ester, a nitrile group or a carboxyl group;

$R^4$ denotes an amide, such as, for example, an unsubstituted amide or a mono- or dialkylamide having 1 to 3 carbon atoms per alkyl radical, an ester, such as, for example, an alkyl ester having 1 to 4 carbon atoms per alkyl radical, a benzyl ester, a nitrile group a carboxyl group, nitro, alkylsulphinyl having 1 to 4 carbon atoms, phenylsulphinyl, alkylsulphonyl having 1 to 4 carbon atoms, phenylsulphonyl, alkylcarbonyl having 1 to 6 carbon atoms in the alkyl part, trifluoromethyl-carbonyl, phenylcarbonyl, dicyanomethylene, formylvinyl, alkoxycarbonylvinyl having 1 to 6 carbon atoms in the alkoxy part, or a carbonyl group which is substituted by a pyrrole radical;

$R^5$ denotes hydrogen, alkyl having 1 to 5 carbon atoms, phenyl, phenyl which is substituted by up to three alkoxy groups having 1 to 4 carbon atoms, a radical which is derived from 5-oxo-perhydro-1,4-thiazepine, or amino;

$R^6$ denotes hydrogen, it also being possible for $R^5$ and $R^6$, together with the

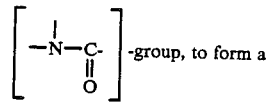

-group, to form a 2-pyrrolidinone-ring; and pharmaceutically acceptable salts and acid addition salts thereof.

2. Pharmaceutical composition characterized in that it contains, as the active compound, a pyrrole compound according to claim 1 together with a pharmaceutically acceptable excipient and, optionally, pharmaceutically acceptable additive and other pharmacological active compounds.

3. Pyrrole derivatives according to claim 1 characterized in that the carboxylic acid groupings $R^3$ or $R^4$ are amides, such as, for example, unsubstituted amide or mono- or dialkyladides having 1 to 3 carbon atoms per alkyl radical, esters, such as, for example, alkyl esters having 1 to 4 carbon atoms per alkyl radical or benzyl esters, the nitrile group or the carboxyl group.

4. Method for combating or preventing diseases caused by a restriction in cerebral function and/or for treating or combating cerebral aging processes, which comprises administering an effective dose of a compound of claim 1 to a patient in need thereof.

* * * * *

UNITED STATES PATENT AND TRADEMARK OFFICE
CERTIFICATE OF CORRECTION

PATENT NO. : 4,966,901
DATED : October 30, 1990
INVENTOR(S) : Zoller et al.

It is certified that error appears in the above-identified patent and that said Letters Patent is hereby corrected as shown below:

col. 4, line 18, "thiocarbon-ylamino" should read --thiocarbonylamino--;

col. 13, line 7, "2propenoate" should read --2-propenoate--;

col. 14, line 46, "O 0 14.4" should read --O 14.4--;

col. 15, line 11, "O 3.2" should read --O 13.2--;

col. 18, line 8, "27, 27" should read --27, 37--;

In the claims:

Claim 1, col. 19, line 42, ";II" should read --II;--
Claim 1, col. 20, line 8, before "a" insert a comma --,--;
Claim 3, line 4 thereof, "dialkyladides" should read --dialkylamides--.

Signed and Sealed this

Nineteenth Day of May, 1992

Attest:

DOUGLAS B. COMER

Attesting Officer

Acting Commissioner of Patents and Trademarks